(12) United States Patent
Bagga et al.

(10) Patent No.: US 7,198,627 B2
(45) Date of Patent: Apr. 3, 2007

(54) SPINAL FIXATION DEVICE AND METHOD

(75) Inventors: Charanpreet Bagga, Phoenixville, PA (US); Eric Gray, Colorado Springs, CO (US); Carlo Ventre, Turbenthal (CH)

(73) Assignee: Zimmer Spine, Inc., Minneapolis, MN (US)

( * ) Notice: Subject to any disclaimer, the term of this patent is extended or adjusted under 35 U.S.C. 154(b) by 535 days.

(21) Appl. No.: 10/235,227

(22) Filed: Sep. 4, 2002
(Under 37 CFR 1.47)

(65) Prior Publication Data
US 2003/0144666 A1 Jul. 31, 2003

Related U.S. Application Data

(60) Provisional application No. 60/317,889, filed on Sep. 7, 2001.

(51) Int. Cl.
*A61B 17/70* (2006.01)

(52) U.S. Cl. ...................................................... 606/61

(58) Field of Classification Search ................ 606/61, 606/54, 53, 69, 70, 71, 72, 73, 86, 104
See application file for complete search history.

(56) References Cited

U.S. PATENT DOCUMENTS

| | | | |
|---|---|---|---|
| 5,147,361 A * | 9/1992 | Ojima et al. .................. 606/61 |
| 5,282,863 A | 2/1994 | Burton | |
| 5,300,073 A * | 4/1994 | Ray et al. ..................... 606/61 |
| 5,324,290 A * | 6/1994 | Zdeblick et al. ............... 606/61 |
| 5,429,639 A * | 7/1995 | Judet ............................ 606/61 |
| 5,531,746 A * | 7/1996 | Errico et al. .................. 606/61 |
| 5,549,608 A | 8/1996 | Errico et al. | |
| 5,586,984 A | 12/1996 | Errico et al. | |
| 5,607,426 A * | 3/1997 | Ralph et al. .................. 606/61 |
| 5,676,666 A | 10/1997 | Oxland et al. | |
| 5,868,749 A | 2/1999 | Reed | |
| 5,968,047 A | 10/1999 | Reed | |
| 6,010,503 A | 1/2000 | Richelsoph et al. | |
| 6,022,350 A * | 2/2000 | Ganem ......................... 606/61 |
| 6,056,749 A | 5/2000 | Kuslich | |
| 6,398,783 B1 | 6/2002 | Michelson | |
| 6,599,290 B2 * | 7/2003 | Bailey et al. ................. 606/69 |

FOREIGN PATENT DOCUMENTS

FR    0625337 A1 *  5/1994

OTHER PUBLICATIONS

Dubois, et al. *Dynamic Neutralization: A New Concept for Restabilization of the Spine*, from "Lumbar Segmental Instability" pp. 233-240, Lippincott Williams & Wilkins Healthcare, 1999.
Dynesys™ brochure, Sulzer Orthopedics Ltd. 1998.
Scharer, et al *Static and Dynamic Biomechanical tests of a Dynamic Neutralization System for the Spine*, ESS 98 Innsbruck.

* cited by examiner

*Primary Examiner*—Eduardo C. Robert
*Assistant Examiner*—David Comstock
(74) *Attorney, Agent, or Firm*—Faegre & Benson LLP

(57) ABSTRACT

A fixation device and method stabilizers at least one bone of a patient. The device includes a connector with one end defining a screw fixator configured to receive an anchoring screw and a securing cap configured to maintain the screw in the screw fixator.

7 Claims, 9 Drawing Sheets

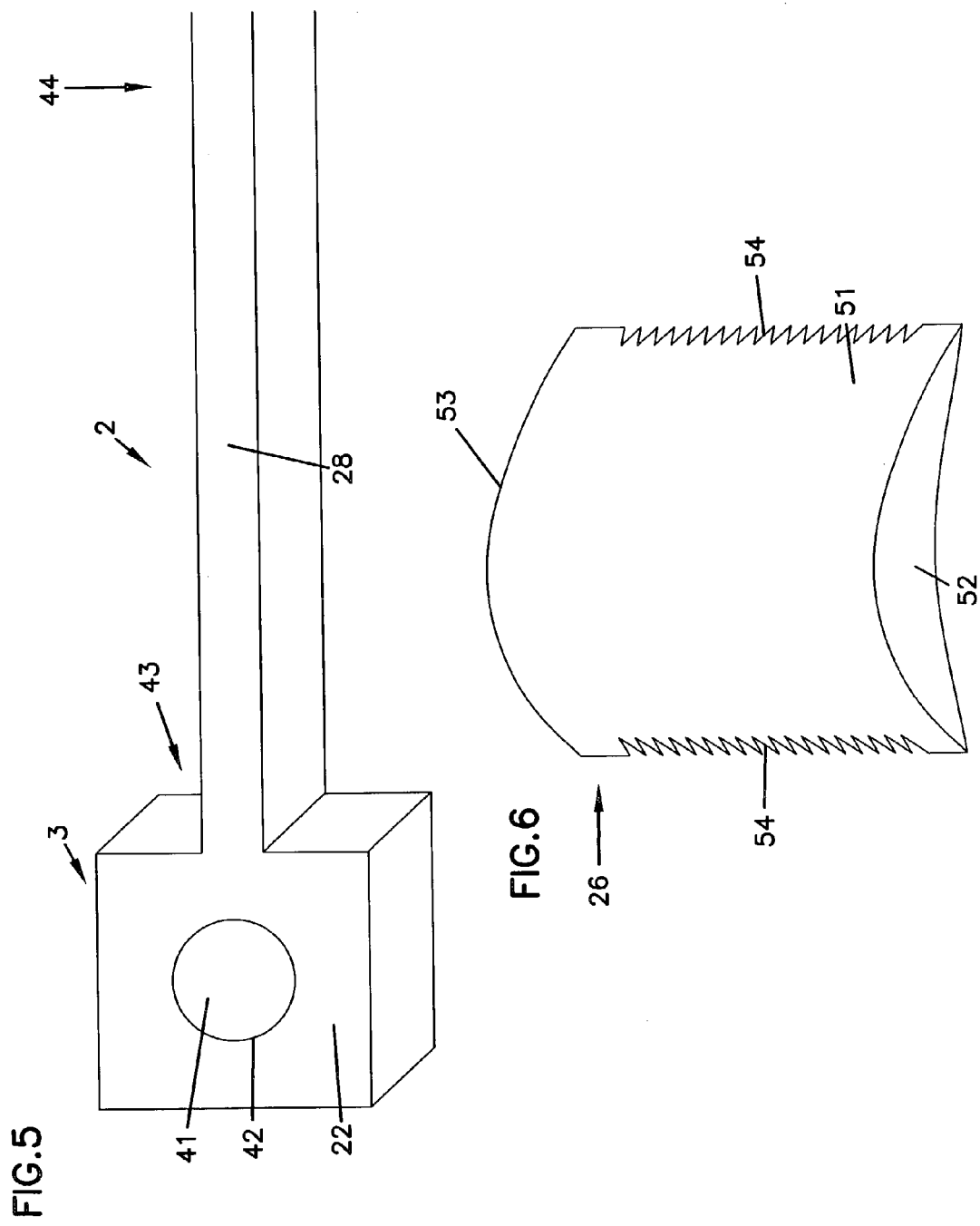

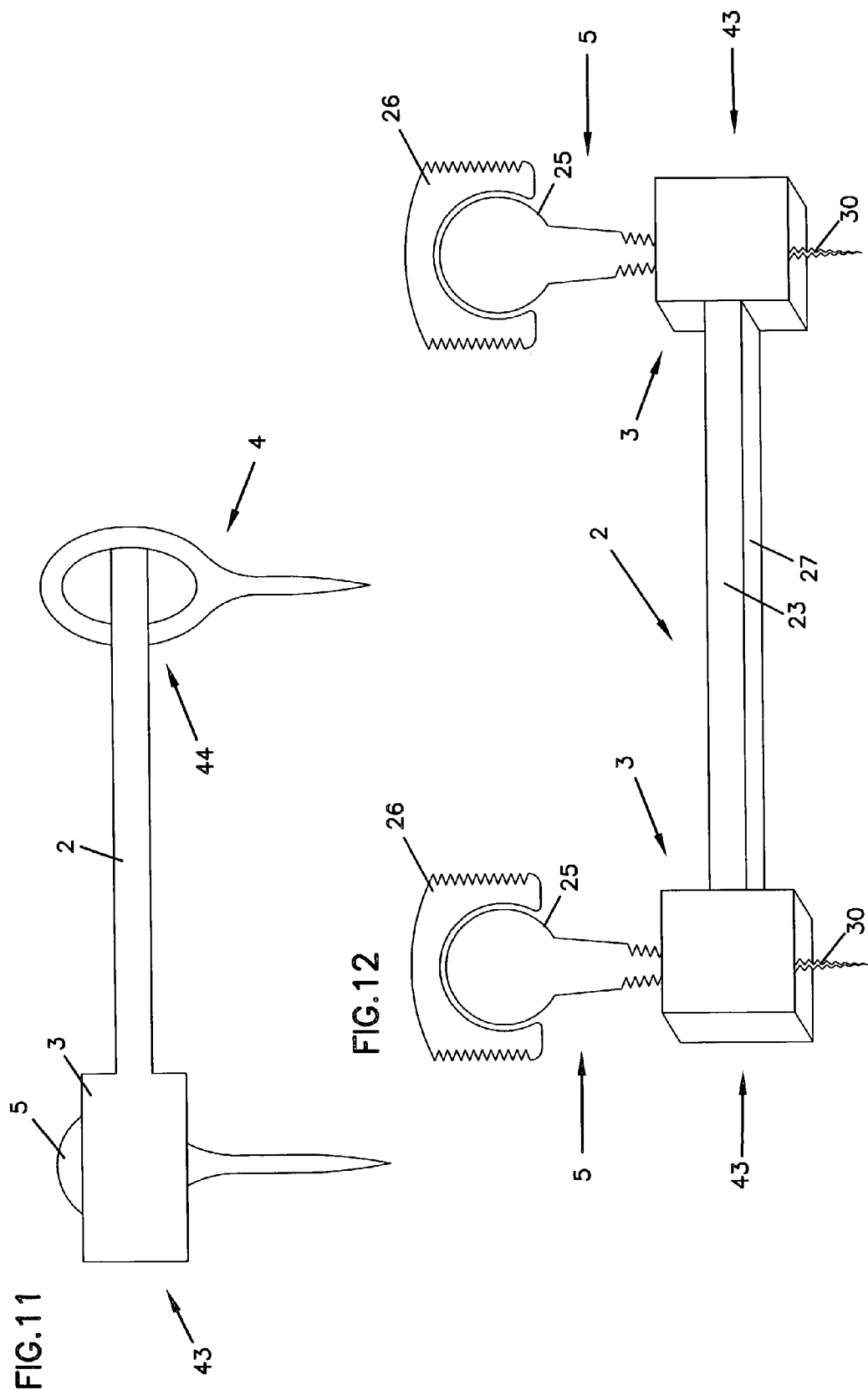

SPINAL FIXATION DEVICE AND METHOD

CROSS-REFERENCE TO RELATED APPLICATIONS

This application claims the benefit of U.S. Provisional Application 60/317,889, filed Sep. 7, 2001.

BACKGROUND

The human spinal column is prone to diseases that produce disruption of the normal architecture of the spine. These conditions of the spine include those involving vertebral displacement such as kyphosis, segmental instability such as degenerative disc disease, and fractures caused by trauma. Frequently, treatment of these spinal disorders involves spinal stabilization, for example, by immobilization of the affected vertebral joint(s) via internal surgical fusion, a process that typically includes the attachment of implants to the spinal vertebrae and securing the implants to spinal rods.

SUMMARY

The invention provides a fixation device, suitable for fixing the positioning of at least one bone of a patient. Generally, the device includes a connector with one end defining a screw fixator configured to receive an anchoring screw and a securing cap configured to maintain the screw in the screw fixator.

BRIEF DESCRIPTION

Additional features of the present invention will be apparent to those skilled in the art from the following detailed description when considered in conjunction with the accompanying drawings, wherein:

FIG. 5 is a top view of a screw fixator.

FIG. 6 is a perspective view of a securing cap.

FIG. 11 is a view of the fixation device showing the anchoring screw and the secondary screw.

FIG. 12 is a side view of a fixation device having a screw fixator at both ends.

DETAILED DESCRIPTION

Figure 1:
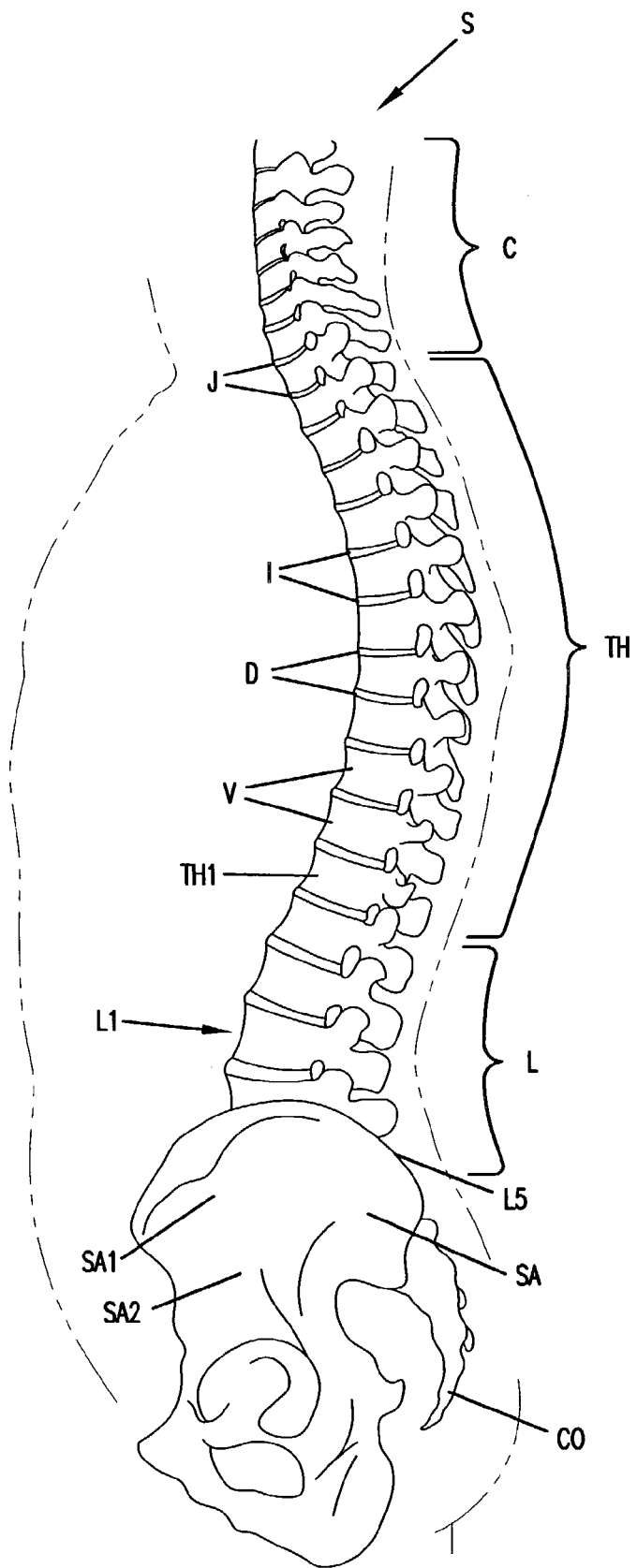
FIG. 1 is a lateral view of the vertebral column showing its normal curvatures (cervical, thoracic, lumbar, sacrococcygeal) and its relationship to the hip bone.

To facilitate a better understanding of the present invention, description will first be made of a spinal fixation system and related insertion method. In the drawings, similar elements are labeled similarly throughout.

A. Anatomy of the Spine.

1. Overview.

The human spine (spinal column) S and vertebra V (see, generally FIGS. 1, 2) will now be described to facilitate an understanding of the present invention. The spine S is a flexible column formed of a series of bones called vertebrae V. The spine provides a partly rigid and partly flexible axis for the body with important roles in posture, support of body weight, locomotion and protection of the spinal cord. In humans, the spine S (also referred to as the spinal column) generally includes 33 vertebrae, separated into five regions, cervical C, thoracic TH, lumbar L, sacral SA and coccygeal CO. Typically, the vertebrae in the cervical C, thoracic TH and lumbar L regions of the spine are separated; but those found in the sacral SA and coccygeal CO regions are typically fused, so as to form two bones—the upper bone or sacrum SA, and the lower or terminal bone of the spine, the coccyx CO. The bodies of the vertebrae are piled one upon the other, forming a pillar to support the cranium and trunk.

Viewed laterally, a typical human spinal column has several curves that generally correspond to the different regions of the column. For example, the lumbar curve L1 generally commences at the middle of the last thoracic vertebra TH 1 and terminates at the sacro-vertebral angle SA 1. It is generally convex anteriorly, with the convexity of the lower three lumbar vertebrae typically much greater than that of the upper two.

Figure 2:
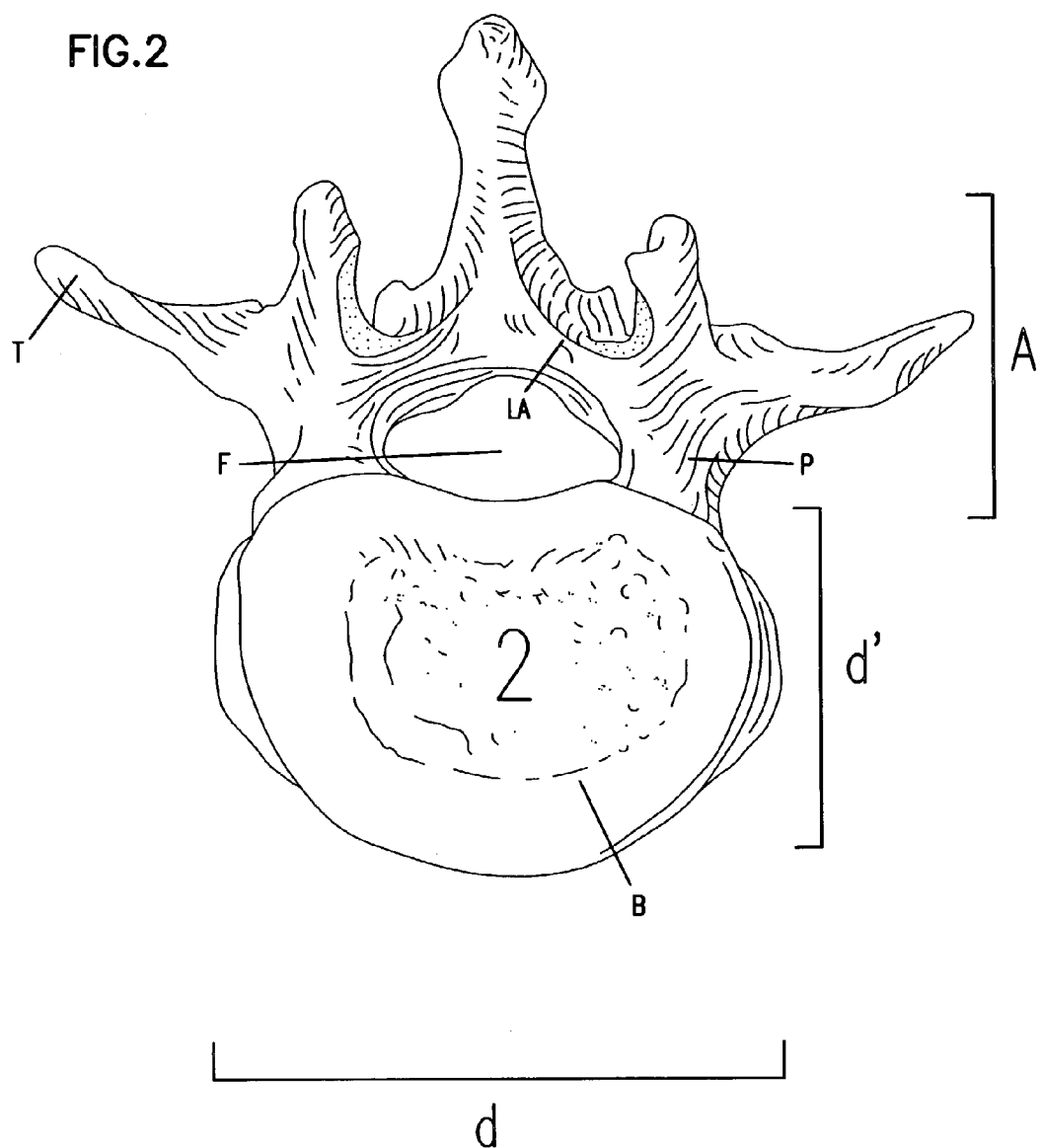
FIG. 2 is the superior view of a typical lumbar vertebra.

Referring to FIG. 2, the individual vertebrae V of the spine S include a body B and various spinal processes, such as the pedicle P, the lamina LA and the transverse process T. The vertebral pedicles P are two short pieces of bone, which project backward, one on each side, from the upper part of the body of the vertebra, at the line of junction of its posterior and lateral surfaces. The spinal processes (also referred to as vertebral arches A) form a vertebral foramen F behind the body(ies) B of the vertebrae V which encompasses and protects the spinal cord.

Referring to FIG. 1, the connection between adjacent bones is called a joint or articulation. Adjacent vertebrae V are connected by an intervertebral joint J, which provides movement in combination with strength. The intervertebral joint J is made up of intervertebral discs and ligaments (including the anterior longitudinal ligament and posterior longitudinal ligament). The intervertebral discs D, are plates of fibrocartilage that have an external anulus fibrosus, which surrounds an internal gelatinous nucleus pulposus.

2. Lumbar Vertebrae

The lumbar vertebrae L account for much of the thickness of the lower trunk in the median plane. In the lumbar region, the vertebral pedicles are very strong, directed backward from the upper part of the bodies. As best shown in FIG. 2, the body B of a lumbar vertebra L is generally larger than the bodies of vertebrae from other regions of the spine. The body B generally has a lateral diameter d (from side to side) that is greater than the diameter from anterior to posterior d', providing a broad basis for the support of the superincumbent weight.

3. The Sacrum.

Referring to FIG. 1, the sacrum SA is a large, generally triangular bone formed from five fused sacral vertebrae. It is situated at the lower part of the spinal column S and at the upper and back part of the pelvic cavity. Its upper part or base SA 2 articulates with the last lumbar vertebra L5.

B. Vertebral Disease.

In general, diseases of the spine cause disruption of the anatomical and functional relationship between adjacent vertebrae. Diseases or conditions affecting the lower regions of the spine, particularly the lumbar-sacral area may cause anatomical or functional disruption between the point of connection between the spine and its major support structure, the pelvis. Lumbar sacral stabilization may correct various disorders of this anatomical region, such as the displacement of the lumbar vertebrae, degeneration of the intervertebral spaces and fractures of the lumbar spine or sacrum.

C. Fixation Systems.

The invention relates generally to an apparatus and methods for the management of spinal conditions that may produce instability or deformity. Stability can be increased by fusing the vertebrae to each other or by fusing the lumbar vertebrae to the sacrum. As used herein, the term 'fusion' refers to internal fixation of the intervertebral joints to reduce relative movement between the vertebrae. Internal fixation can provide stability in such conditions as vertebral fractures, vertebral body tumors, post traumatic kyphosis and congenital kyphosis.

Having described the characteristics and problems of vertebral disease, a treatment apparatus and device will be described.

D. Overview of the Spinal Fusion Implant Process.

Bone fixation devices can include an elongate rod secured to one or more selected vertebrae. Typically, spinal fixation mechanisms include a screw, such as a pedicle screw, secured to a rod. For example, one internal spinal fixation mechanism includes an elongate transpedicular rod or plate having spaced apertures though which one or more screws are inserted. The screws are fixed to the elongated rod or plate and held in place by a fastening mechanism, such as a nut.

E. Issues Relating to Spinal Implants.

1. Implant Size

Typically, pedicle screws are inserted into selected vertebral bodies and are attached to the connector rod. For example, the upper portion of each pedicle screw includes an aperture through which the spinal rod extends, and is held in place by a corresponding connector such as a nut. The nut normally projects beyond the head of the screw.

Components that are large or bulky, such as the projecting nut and the upper portion of the pedicle screw, can cause irritation of soft tissues in the vicinity of the implant.

2. Screw Position

A second issue of concern relates to the position of the pedicle screw. Transpedicular fixation systems generally include one or more parallel elongate rods which are secured to one or more pedicle screws. Typical transpedicular fixation systems, whether 'top loading' (surgeon tightens appliance connections from the top of the plate) or 'side loading' (tightening of the set screws from the side), may not permit the surgeon to vary or control the angulation of the screws segment by segment. Thus, the screws may be forced into a non-anatomic position.

3. Screw Breakage

It is generally preferable to conform the rod to the curvature of the spine, such that the screw is oriented in a direction perpendicular to the surface of the bone (e.g., the pedicle). Variance from a perpendicular relationship may result in constant unidirectional torque of the screw against one surface of the hole in the pedicle receiving the screw. The constant torque may, in turn, cause weakening or breakage of the screw, erosion of the bone or undesirable shifting of the vertebrae-to-adjacent-vertebrae angular relationship.

4. Manipulation of the Implant During Placement

During implantation, the surgeon typically performs multiple contouring steps to insert the pedicle screws in the appropriate location, place the spinal rod in the desired position and secure the rod to the seated pedicle screws. A bulky rod locking mechanism may increase the manipulation required by the surgeon. This, in turn, may increase the difficulty of the procedure, and extend the duration of the surgery, possibly increasing the risk of intra-operative and post-operative complications. For example, a wider surgical incision may be required to place a bulky device, thereby increasing the risk of hemorrhage and infections ultimately delaying healing.

4. Other Bones.

In addition to disorders affecting vertebral position and orientation, surgeons may treat fractures of skeletal bones. As used herein, the term "skeletal bone" refers to bones that are not part of the spinal column S including, but not limited to, the long bones such as the femur, tibia, fibula, humerus, radius and ulnar. Similar considerations discussed with respect to spinal implants apply in these cases.

F. Description of the Apparatus.

The following discussion describes one embodiment of a fusion device of the invention with reference to implanting the device between adjacent vertebrae V or between lumbar vertebrae L and the sacrum S. However, this description is for explanatory purposes only. As stated above, the devices disclosed herein can be used at other joints or locations to facilitate bone fusion.

Figure 3:
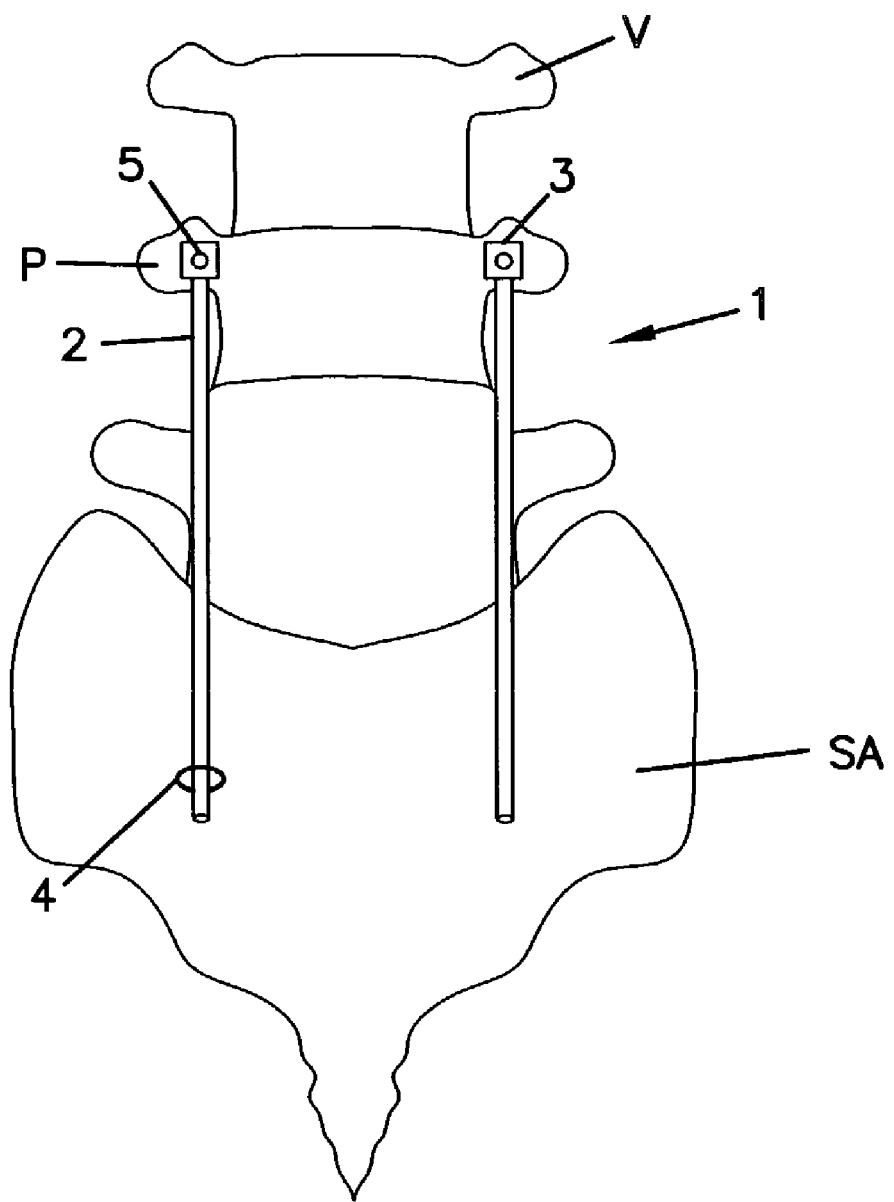
FIG. 3 is an elevational view of a spinal fixation device, according to the invention, connected to vertebral bodies of a spinal column.

With reference to FIG. 3, an embodiment of the invention is shown stabilizing the vertebrae V of a spinal column S by securing the device to one or more vertebrae V and the sacrum SA. A portion of the spinal column S is shown, including a plurality of lumbar vertebrae V and sacrum SA.

1. Elongate Connector

In general, the spinal fixation device 1 includes an elongate connector 2 configured to be secured to at least one bone of a patient. As shown in FIG. 3, the device 1 can be operably connected to one or more vertebrae V at the pedicle portions P thereof.

The elongate connector 2 is secured to at least one bone of a patient in a manner that maintains a desired relative position between the vertebrae V. For example, the elongate connector can be secured using one or more screws. In one embodiment, a single device is used. In another embodiment, more than one device is used. For example, two devices can be used, one on each side of the spinal column as shown in FIG. 3.

Figure 7:
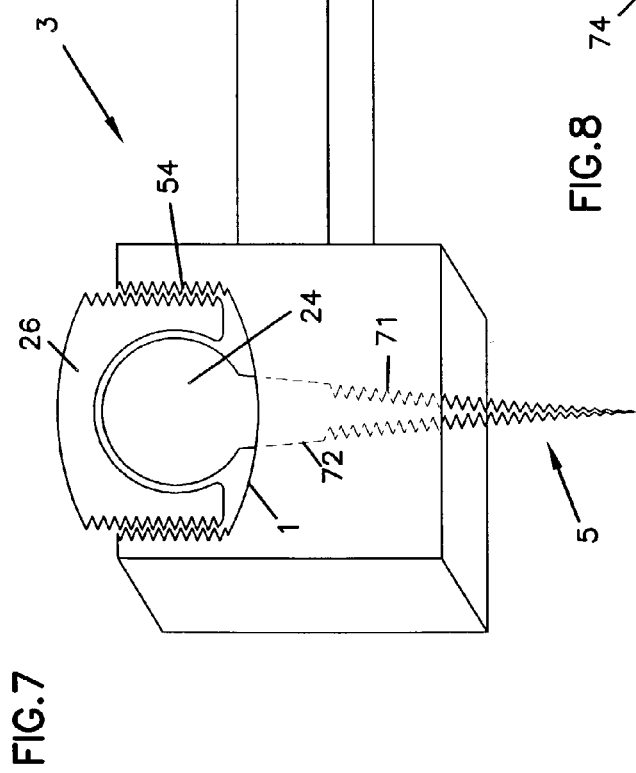
FIG. 7 is a cross sectional view of a screw fixator and pedicle securing cap.

As shown in FIGS. 5 and 7, the elongate connector 2 has a first end 43 and a second end 44. In cross-section, the elongate connector 2 may be any suitable shape such as circular, tangential, square, rectangular or ellipsoid. (See FIGS. 4 and 4A) The elongate connector 2 (see, in general, FIGS. 4 and 5) has as a first surface 27 that is directed toward the vertebrae V, when the device is in use and a second surface 28 that is directed away from the vertebrae V, when the device is in use.

Figure 4:
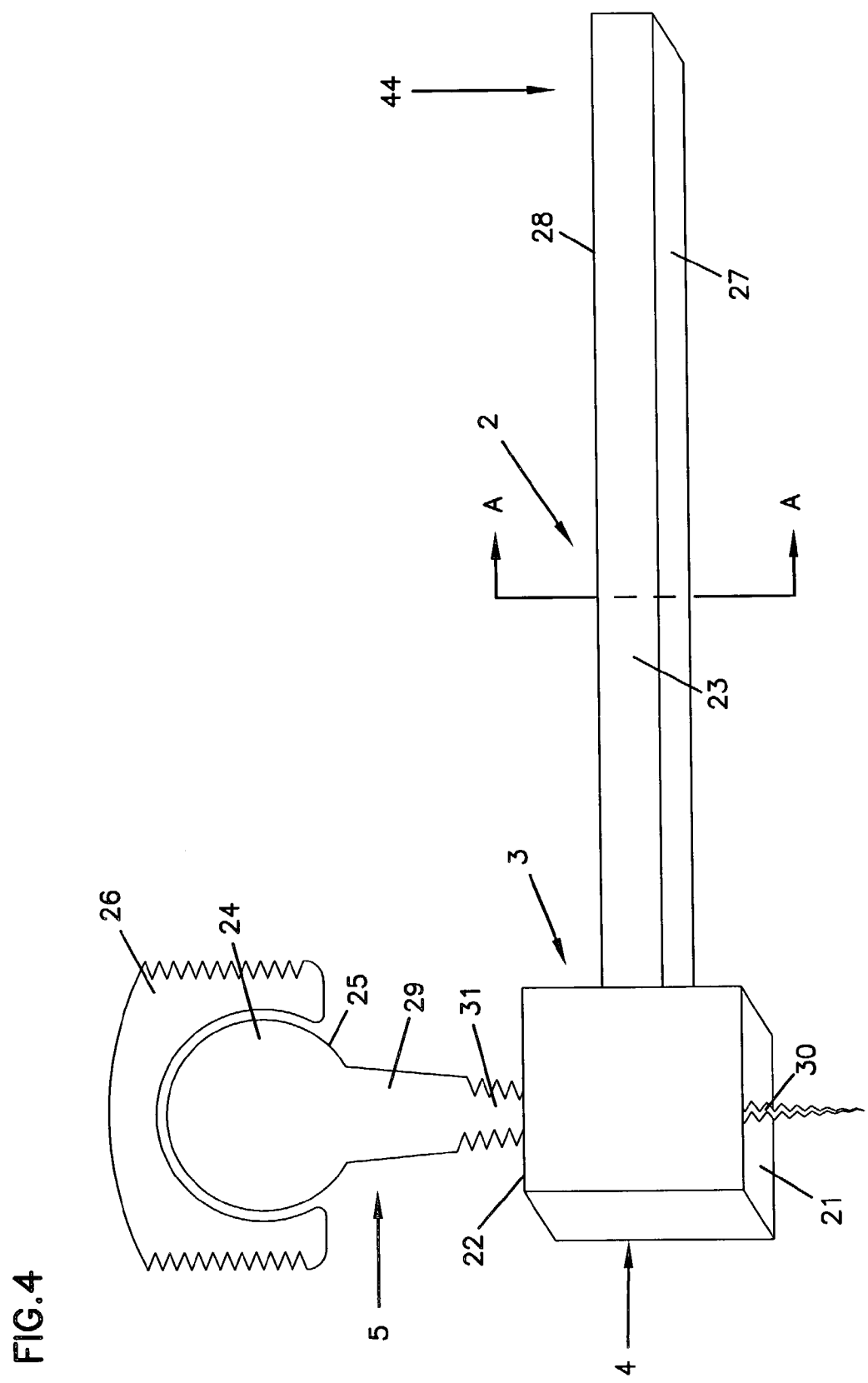
FIG. 4 is an exploded side view of the fixation device in FIG. 3.
Figure 4A:
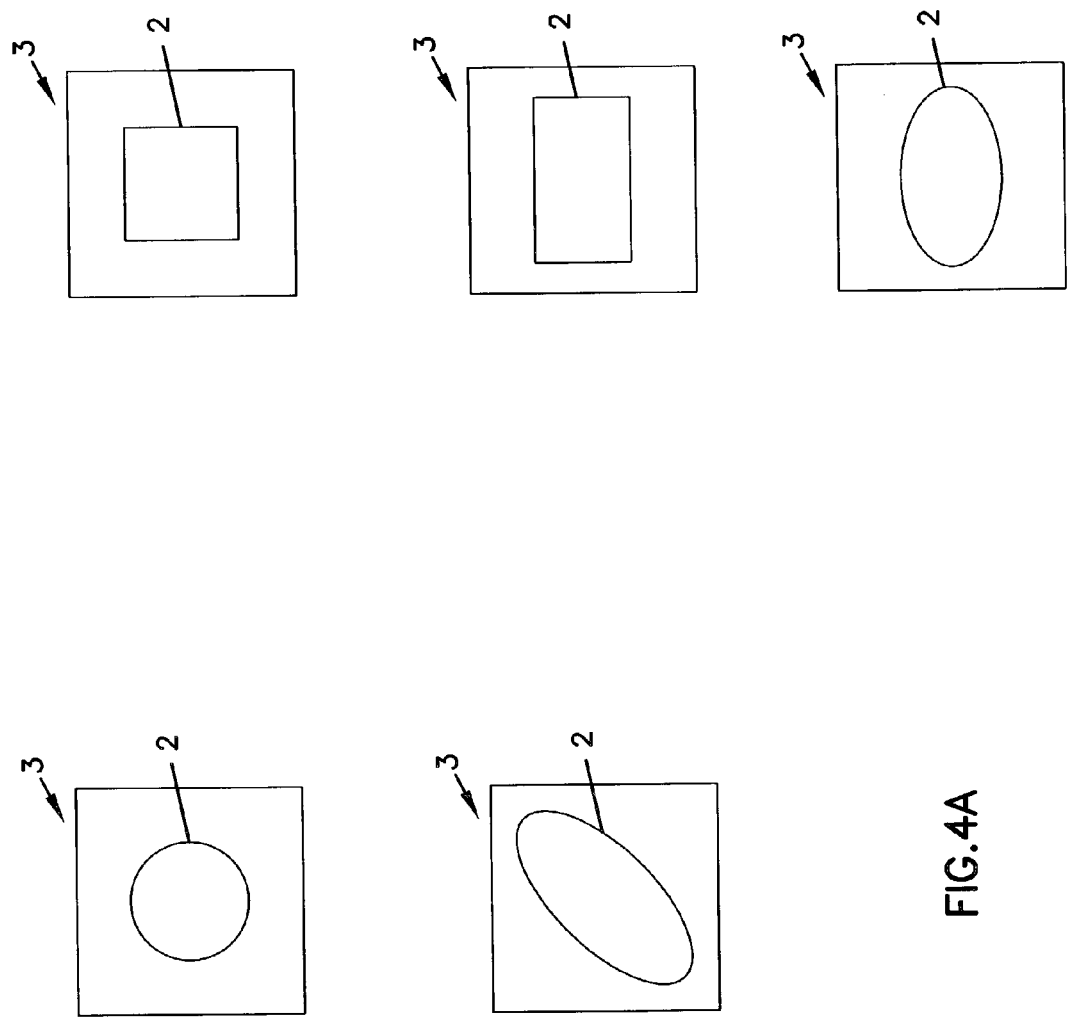
FIG. 4A is a cross-sectional view of the elongate connector.

In the embodiment of FIGS. 3–5, according to the invention, the first end 43 of the elongate connector 2 defines a screw fixator 3. In one embodiment (not shown), the second end 44 defines a screw fixator 3. In an alternate embodiment, the second end 44 of the elongate connector 2 is configured to engage a secondary screw 4. Depending on the type of secondary screw 4, it may be desirable to include one or more apertures (not shown) from the first side 27 to the second side 28 of the elongate connector 2 along the length of the elongate connector 2, wherein each aperture is configured to receive a secondary screw 4.

The elongate connector 2 may be constructed in various manners and sizes depending on the size of the patient and the desired stabilization effect.

The elongate connector 2 and the screw fixator 3 are machined out of biologically inert materials capable of surgical sterilization. Suitable materials include metals and metal alloys, such as titanium, stainless steel, cobalt-chromium, titanium alloys; superelastic materials such as nitinol; plastics and plastic composites; carbon graphite; and ceramic; etc.

3. Screw Fixator

According to the invention, at least one end of the elongate connector 2 defines a screw fixator 3, which is configured to receive an anchoring screw. In one embodiment, the screw fixator 3 and the elongate connector 2 are integrally formed as a single piece. Alternatively, the screw fixator 3 and elongate connector 2 can be formed separately and joined by any suitable method, for example, welding, screws, rivets, etc.

The screw fixator 3 (see, in general FIGS. 3, 4, and 7) has a first major side surface 21 configured to face the vertebra when the device is in use. The screw fixator 3 also has a second major side surface 22, on a side opposite the first major side surface, which extends in a direction generally parallel to the first major side surface 21 and is generally oriented away from the vertebra when in use. The major side surfaces are connected by a plurality of minor side surfaces. In one embodiment, the first major side surface 21 is contoured to conform to the surface of the vertebra V.

Figure 8:
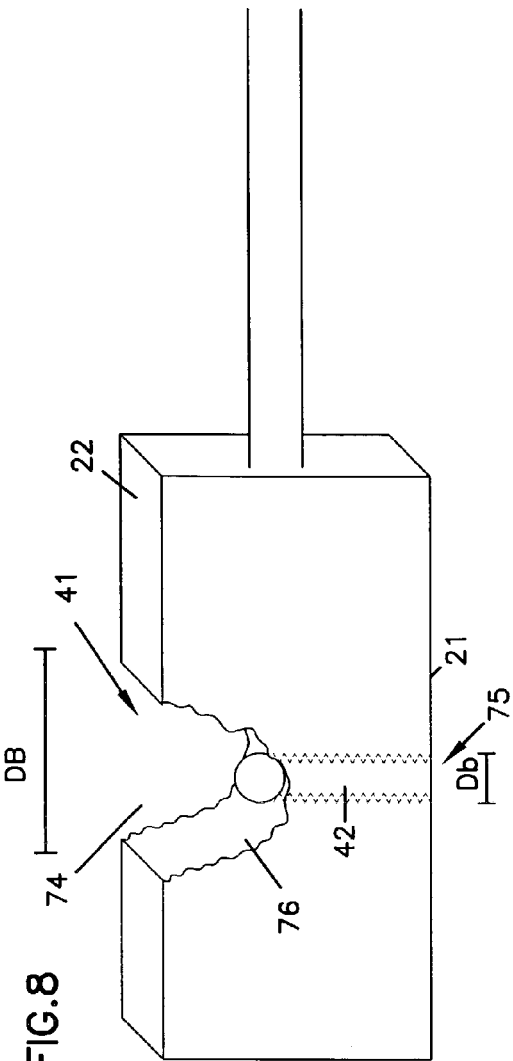
FIG. 8 is a cross sectional view of a screw fixator.

The major side surfaces 21 and 22 of the screw fixator 3 define an opening 41 configured to receive an anchoring screw 5 (See FIGS. 7, 8). An inner surface 42 of the opening 41 extends from the first side surface 21 to the second side surface 22.

In one embodiment the inner diameter (DB) of the opening 41, proximate the second side surface 22 is greater than the inner diameter (Db) of the opening proximate the first side surface 21. The opening proximate the second side surface 22 can thus be referred to as the major opening 74 (i.e., a pocket, recess or countersink) and the opening proximate first side surface can be referred to as the minor opening 75. Generally, the major opening 74 is configured to accommodate at least part of the head 24 of the anchoring screw 5 and the minor opening 75 is configured to accommodate the upper segment 29 of the shaft 31 of the anchoring screw 5. In one embodiment, the inner diameter DB of the major opening 74 is relatively constant, as is the inner diameter Db of the minor opening 75, such that, at the point where the two openings abut, a floor 76 is formed in the major opening. In another embodiment, the floor 76 of the major opening 74, where the major opening 74 abuts the minor opening 75 can be concave. In an alternate embodiment, the inner diameter DB of the major opening 74 gradually decreases as it approaches the minor opening 75, such that the opening 41 extending from the first side surface 21 to the second side surface 22 is frustoconical in shape.

In one embodiment, the entire inner surface 42 of the opening 41 extending from the first major surface side 21 to the second major surface side 22 is threaded. In another embodiment, the inner surface 42 of the opening 41 that is configured to receive the screw head 24 is threaded 71, while the remainder of the opening 72 that is configured to receive the upper segment 29 of the shaft 31 of the anchoring screw 5 is not (See, FIGS. 7,8).

3. Anchoring Screw

The device also includes an anchoring screw 5 which can be coupled to the screw fixator 3 to secure the fixation device 1 to at least one bone of a patient. Generally, the anchoring screw 5 is sized to extend through the screw fixator 3 and into the bone of the patient. In one embodiment, the anchoring screw 5 is configured to secure the fixation device 1 to the pedicle P or transverse process T of a vertebra V. (See, for example, FIG. 2)

Referring to FIG. 4, an anchoring screw 5 generally includes a head 24 and a shaft 31. Typically, at least a part of the shaft 31 (not shown) is textured to enhance frictional engagement with the bone to which it is secured. For example, the shaft can be included a helically wound thread (i.e., a screw) or other textures, such as ridges or knurls. Generally, the shaft 31 include a upper shaft 29, extending from a position at or around the midline of the shaft 31 towards the head 24 of the screw 5 and a lower shaft 30, extending from a position at or around the midline of the shaft 31 away from the head 24 of the screw 5. Generally, the upper shaft 29 engages the opening 41 of the screw fixator 3 and the lower shaft 30 engages the bone of the patient. The upper shaft 29 therefore has a diameter that is the same as or less than the diameter of the opening 41 in the screw fixator 3. Preferably, the upper shaft 29 has a diameter that is less than the diameter of the opening 41. More preferably, the upper shaft 29 has a diameter that is less than the diameter of the minor opening 75.

Typically, the lower shaft 30 is textured to enhance frictional engagement of the screw 5 with the bone. (See, FIG. 4) Examples of suitable textures include helical threads, ridges or knurls. If desired, both the upper 29 and lower 30 shaft can be textured. Other configurations are envisioned, for example, the lower shaft 30 may include a clip mechanism that can be deployed after the screw is inserted into the vertebrae.

Figure 10:
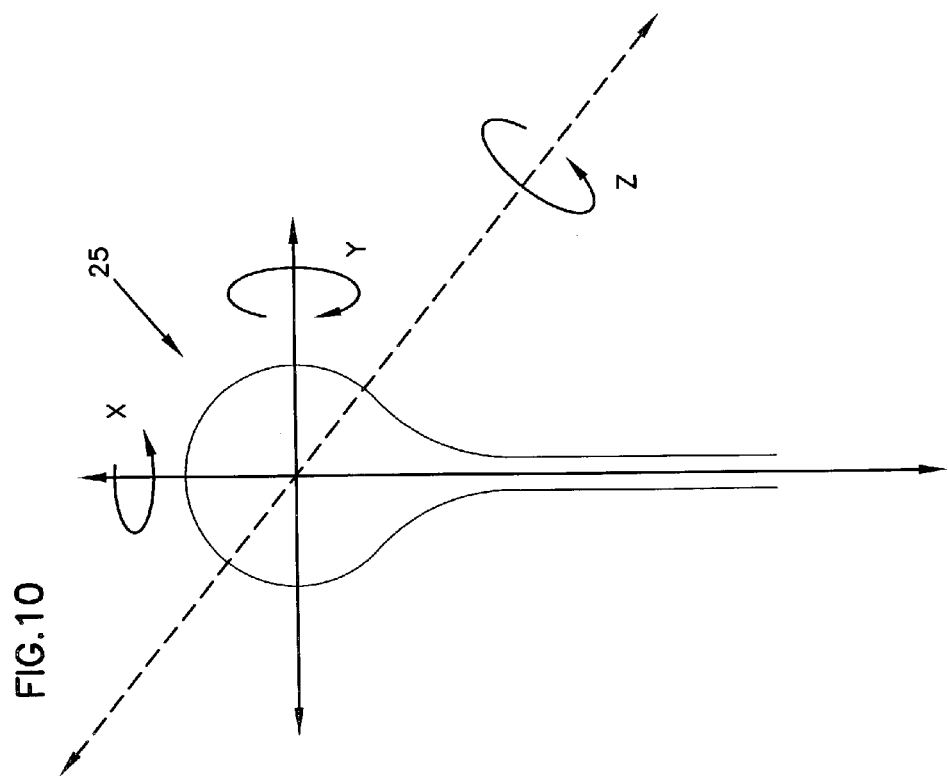
FIG. 10 is a view of an anchoring screw showing directions of perpendicular axes X, Y, Z.

Generally, the head 24 of the screw 5 is configured and sized such that at least a portion of the head 24 of the anchoring screw 5 is contained within the screw fixator 3. In one embodiment, the entire head 24 of the anchoring screw 5 is recessed within the opening 41 of the screw fixator 3 once fully implanted. Preferably, the head 24 of the anchoring screw 5 is curved or spherical to facilitate rotation of the screw fixator 3 and the elongate connector 2 around the head of the screw 5. Preferably, the elongate member 2 and screw fixator 3 can be rotated around the head 24 of the screw 5 to create movement in at least one of three, mutually perpendicular, dimensions X, Y or Z, similar in function to a ball and socket joint. (See FIG. 10)

If the screw fixator 3 has a major opening 74 that abuts a minor opening 75 at a floor 76, the anchoring screw can be configured such that the base 25 of the head 24 rests on the floor 76 when in place.

The mobility of the "ball and socket joint" allows the surgeon to vary or control the angulation of the device 1 to reduce the likelihood that the screw 24 is forced into a non-anatomic position. The "ball and socket" arrangement also reduces the likelihood that the screw 24 is subjected to constant unidirectional torque that may result in weakening and breakage of the screw, erosion of bone or undesirable shifting of the vertebrae-to-adjacent vertebrae angular relationship.

The anchoring screw 24 may be constructed in various manners and in various sizes. The anchoring screw 24 can be manufactured using any suitable biologically compatible materials, preferably one that is capable of surgical sterilization. Suitable materials include metals and metal alloys, such as titanium, stainless steel, cobalt-chromium, titanium alloys; superelastic materials such as nitinol; plastics and plastic composites; carbon graphite; bone; and ceramic; etc.

4. Securing Cap

The device also generally includes a securing cap 26 configured to engage the screw fixator 3 and secure the anchoring screw 5 to the screw fixator 3 (See, in general, FIGS. 4, 6). Generally, the securing cap 26 includes a body 51 having a leading end 52 and a trailing end 53. An external surface 54 extends from the leading end 52 to the trailing end 53. (See, FIG. 6). In one embodiment the leading end 52 has a concave surface configured to engage a rounded head 24 of the anchoring screw 5.

If desired, the external surface 54 of the securing cap 26 can be threaded with threads having a pitch and diameter corresponding to the threaded inner surface 42 of the opening 41 of the screw fixator 3 (See, FIGS. 8, 6). The threaded inner surface 71 of the opening 41 permits the insertion of a securing cap 26 with subsequent tightening/locking of the securing cap 26 within the screw fixator 3.

In an alternate embodiment, the securing cap 26 is secured to the screw fixator 3 by other mechanisms such as a snap fit, ratchet structure.

Generally, the securing cap 26 is secured to the screw fixator 3, such that the trailing end 53 of the securing cap 26 lies substantially in the same plane as the first major side surface 22 of the screw fixator 3. This arrangement reduces the profile of the implanted fixation device 1, because the upper portion of the anchoring screw 5 is not held in place by a connector such as a nut, which protrudes above the first major side 22 of the screw fixator 3. The reduced profile reduces the likelihood of soft tissue irritation or stress on the facet joints of the vertebrae.

The securing cap 26 may be constructed in various manners and in various sizes. The securing cap 26 can be manufactured using any suitable biologically inert materials, preferably one that is capable of surgical sterilization. Suitable materials include metals and metal alloys, such as titanium, stainless steel, cobalt-chromium, titanium alloys; superelastic materials such as nitinol; plastics and plastic composites; carbon graphite; bone; and ceramic; etc.

5. Secondary Screw

According to the invention, the second end of the elongate connector 2 is operably connected to the same or another bone of a patient as the first end. In one embodiment, the second end of the elongate connector is configured to engage a secondary screw 4 (See FIGS. 3 and 11). Any suitable commercially available screw, for example, commercially available pedicle screws, may be used to secure the second end of the elongate connector 2.

Figure 9:
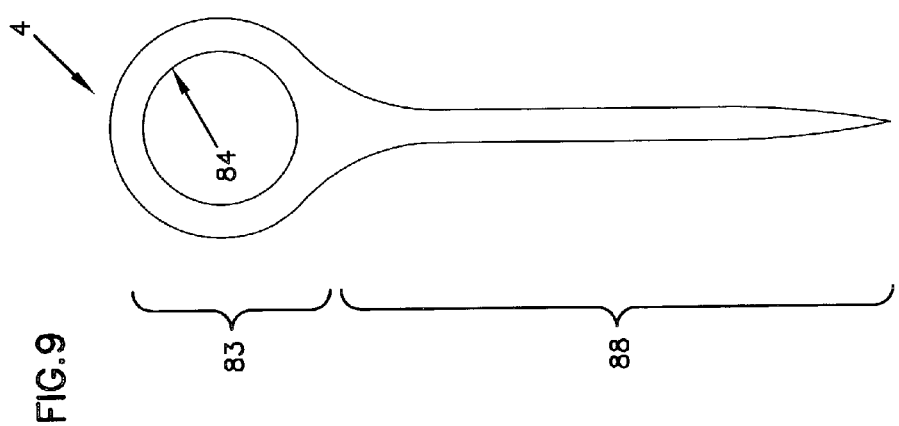
FIG. 9 is an elevational view of a secondary screw.

Referring to FIG. 9, the secondary screw 4 includes a head 83 and a shaft 88. The head 83 is generally configured to engage the elongate connector 2, while the shaft 88 is generally configured to be secured to a patient's bone. In one embodiment, apertures are located along the length of the elongate connector 2, such that one or more secondary screws 4 can be inserted through the aperture and secured to a bone. In another embodiment, the secondary screw 4 includes an engagement member that is configured to receive and secure the elongate connector 2. For example, the head 83 of the secondary screw 4 can be constructed as a loop that is configured to receive the elongate connector 2 (See, FIGS. 9, 11). Alternately, the head 83 of the secondary screw 4 can be configured as a "U" shaped saddle that is adapted to receive the elongate connector 2. A securing device can then be used to secure the elongate connector 2 within the saddle.

The head 83 of the secondary screw 4 is operably connected to the shaft 88. The shaft 88 is configured to engage the bone of a patient. Typically, the shaft 88 is textured to enhance frictional engagement of the screw 4 with the bone. (See, FIG. 4) Examples of suitable textures include helical threads, ridges or knurls. Other configurations are also envisioned, for example, the lower shaft 88 may include a clip mechanism that can be deployed after the screw is inserted into the vertebrae.

The secondary screw 4 may be constructed in various manners and in various sizes. The secondary screw can be manufactured using any suitable biologically inert materials, preferably one that is capable of surgical sterilization. Suitable materials include metals and metal alloys, such as titanium, stainless steel, cobalt-chromium, titanium alloys; superelastic materials such as nitinol; plastics and plastic composites; carbon graphite; bone; and ceramic; etc.

G. The Method of Placement.

The device of the invention can be used to stabilize one or more bones of a patient. Although the method is described below in connection with stabilizing one or more adjacent vertebrae, the method is suitable for use in stabilizing other bones, such as skeletal bones.

In practicing the method, the bone that is to be stabilized is first accessed. For example, the spinal column can be accessed, by a midline posterior approach. Suitable procedures are known.

After the bone is accessible, the first end 43 of the elongate connector 2 is secured to the bone. To do so, an anchoring screw 5 is inserted into the opening 41 defined by the screw fixator 3. The shaft 31 of the anchoring screw 5 is secured to the bone by, for example, threadably advancement therein. For example, the shaft 31 can be secured to the pedicle P of a vertebrae V. Once the anchoring screw 5 is within the screw fixator 3 secured, the elongate connector 2 is positioned along the spinal column S. The anchoring screw 5 is secured by engaging a securing cap 26 to the pedicle screw fixator 3 (See, generally, FIGS. 4, 3). The second end 44 of the elongate connector 2 is then secured to the same or another bone via a secondary screw, or a similar screw fixator 3 and anchoring screw 5 arrangement.

Preferably, the relative curvature of the head and floor allow angular orientation of connector 2 to be adjusted after fixation screw is in place.

The patient is then closed with the device in place.

Having now described the present invention, it will be apparent to one of ordinary skill in the art that many changes and modifications can be made in the invention without departing from the spirit or scope of the appended claims.

What is claimed is:

1. A method for stabilizing at least one bone of a patient, comprising:
   securing a bone anchor in a first bone portion of a patient, the bone anchor comprising a head portion having an aperture;
   inserting an anchoring screw into a fixation device, the fixation device comprising:
   a connector comprising a first end and a second end, the first end defining a screw fixator, wherein the screw fixator defines an opening configured to receive an anchoring screw, the anchoring screw comprising:
   a head adapted to fit at least partially within the screw fixator; and a securing cap;
inserting the second end of the connector through the aperture in the bone anchor;
threading the anchoring screw into a bone of the patient;
advancing the anchoring screw so that the head is recessed within the screw fixator;
securing the securing cap to the screw fixator to secure the anchoring screw; and
permitting the connector to move relative to the bone anchor while maintaining a portion of the connector inside that aperture.

2. The method of claim 1, further comprising:
providing a secondary screw;
securing the secondary screw to at least one bone of a patient; and
securing the second end of the connector to the secondary screw.

3. The method of claim 2, wherein the anchoring screw is secured to a sacral bone and the secondary screw is secured to a lumbar vertebra.

4. The method of claim 3, further comprising a step of securing the connector to the bone of a patient using more than one secondary screw.

5. The method of claim 1, wherein the one bone is a vertebra.

6. The method of claim 1, wherein the bone is a skeletal bone.

7. The method of claim 1, further comprising:
aligning the connector along the at least one bone, after the step of securing the anchoring screw to the bone.

* * * * *